(12) United States Patent
Lam et al.

(10) Patent No.: US 6,194,399 B1
(45) Date of Patent: Feb. 27, 2001

(54) ARYLDIAMINE DERIVATIVES USEFUL AS ANTIBACTERIAL AGENTS

(75) Inventors: Kelvin Lam, Belmont; Yi Bin Xiang, Acton, both of MA (US)

(73) Assignee: Scriptgen Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/413,409

(22) Filed: Oct. 6, 1999

Related U.S. Application Data

(60) Provisional application No. 60/103,825, filed on Oct. 9, 1998.

(51) Int. Cl.[7] ............ A61K 31/63; A61K 31/135
(52) U.S. Cl. ............ 514/155; 514/646; 514/647; 514/649
(58) Field of Search .................. 514/155, 646, 514/647, 649

(56) References Cited

U.S. PATENT DOCUMENTS

| | | | |
|---|---|---|---|
| 4,829,058 | * | 5/1989 | Seydel et al. ............ 514/155 |
| 4,992,430 | * | 2/1991 | Seydel et al. ............ 514/155 |
| 4,994,105 | | 2/1991 | Burgoyne, Jr. et al. ...... 71/118 |
| 5,084,449 | * | 1/1992 | Seydel et al. ............ 514/155 |

FOREIGN PATENT DOCUMENTS

| | | | |
|---|---|---|---|
| 2 186 586 | 8/1987 | (GB) | ............ C09B/51/00 |
| WO 98/22103 | 5/1998 | (WO) | ............ A61K/31/165 |

OTHER PUBLICATIONS

Kostowski, W. et al., Acta Pol. Pharm., 35:3:379–383, 1978 (abstract).

Ashton, M.J. et al., J. Med. Chem., 39:3343–3356, 1996.

* cited by examiner

Primary Examiner—Kevin E. Weddington
(74) Attorney, Agent, or Firm—Darby & Darby

(57) ABSTRACT

Disclosed are pharmaceutical compositions and formulations comprising the compound:

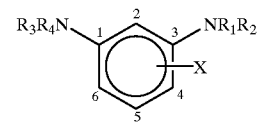

wherein:

(a) $R_1$, $R_2$, $R_3$, and $R_4$ are independently selected from the group consisting of hydrogen, or optionally substituted alkyl, aryl, vinyl, alkyl(aryl), vinyl(aryl), amine, amide; or at least one of $R_1$ and $R_2$, together, and $R_3$ and $R_4$, together, form an optionally substituted ring system, wherein the ring system is optionally interrupted by at least one heteroatom;

(b) X is hydrogen, $NO_2$, CN, halogen, OH, $SO_2$, alkyl, alkoxy, or vinyl; and (c) wherein when $R_1$, $R_2$, $R_3$, and $R_4$ are alkyl, aryl, vinyl, alkyl(aryl), vinyl(aryl), amine or amide, $R_1$, $R_2$, $R_3$, and $R_4$ are optionally interrupted with at least one heteroatom, or a salt thereof; and a pharmaceutically acceptable carrier or diluent. Also disclosed are methods of inhibiting microbial replication and treating microbial infections, comprising administration of a pharmaceutical composition or formulation of the invention.

6 Claims, No Drawings

ARYLDIAMINE DERIVATIVES USEFUL AS ANTIBACTERIAL AGENTS

This patent application claims priority under 35 U.S.C. §119 of U.S. provisional patent application serial No. 60/103,825, filed Oct. 9, 1998, which is incorporated herein by reference.

FIELD OF THE INVENTION

The present invention relates to pharmaceutical compositions comprising aryldiamine derivatives and methods for using aryldiamine derivatives as antibacterial agents. The invention also relates to novel aryldiamine derivatives, their preparation, to pharmaceutical compositions containing them, and to methods of using them to alleviate bacterial infections.

BACKGROUND OF THE INVENTION

New classes of antibacterial agents are needed to address both the growing resistance of bacteria to present therapies and the general lack of efficacy of existing antibiotics against slow-growing organisms. Although bacterial infections were once considered well controlled, the threat posed by the emergence of multidrug-resistant organisms is now well accepted. Desirable characteristics for new antibacterial products include activity against drug resistant organisms, reduced propensity for resistance development, greater biological half-life in humans, reduced liability for allergic reactions, and broad spectrum antibacterial activity.

SUMMARY OF THE INVENTION

The present invention provides pharmaceutical compositions and formulations comprising aryldiamine compounds of generic structure (I):

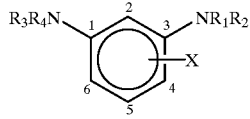

wherein:

(a) $R_1$, $R_2$, $R_3$, and $R_4$ are independently selected from the group consisting of hydrogen, branched or straight-chained $C_1$ to $C_{12}$ alkyl, aryl, vinyl, alkyl(aryl), vinyl (aryl), primary, secondary or tertiary amine, or amide;

(b) X is hydrogen, $NO_2$, CN, halogen, OH, $SO_2$, branched or straight-chained $C_1$–$C_6$ alkyl, alkoxy, or vinyl, positioned on the aromatic ring at any of positions 2, 4,5 or 6;

(c) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, $R_1$, $R_2$, $R_3$, and $R_4$ are optionally interrupted with at least one heteroatom, or optionally substituted with a hydroxy, halogen, nitro, trihalomethyl group, carbonyl moiety, a substituted or unsubstituted, branched or straight-chained $C_1$ to $C_{12}$ alkyl, aryl, vinyl, alkyl(aryl), vinyl(aryl), primary, secondary, or tertiary amine, hydrazone, alkoxy, or aryloxy; and (d) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, optionally at least one of $R_1$ and $R_2$, together, and $R_3$ and $R_4$, together, form a ring system, wherein the ring system is optionally interrupted by at least one heteroatom, and optionally substituted with a hydroxy, halogen, nitro, trihalomethyl group, carbonyl moiety, $C_1$ to $C_{12}$ alkyl, primary, secondary, or tertiary amine, alkoxy, or aryloxy;

or a salt thereof, and a pharmaceutically acceptable carrier or diluent.

In one embodiment, the invention is also directed to novel aryidiamine compounds of structure (I) wherein X is $NO_2$ positioned at the 4-position of the aromatic ring, $R_1$, and $R_3$ are hydrogen, $R_2$ is $-CH_2CH_2OC_6H_5$, and $R_4$ is $-CH_2CH_2NH_2$, or $R_3$ is hydrogen, $R_4$ is $-CH_2CH_2NH_2$, and $NR_1R_2$ is

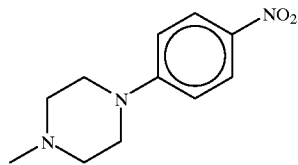

The present invention also provides methods for inhibiting microbial replication and preventing and/or treating microbial infections in an animal, comprising administering an antibacterial effective amount of the pharmaceutical formulations of the invention to an animal in need of such treatment. The microbial infections which may be treated by the composition of the invention include drug resistant microbial infections and multi-drug resistant microbial infections.

DETAILED DESCRIPTION OF THE INVENTION

All patents, patent applications and literature references cited herein are hereby incorporated in their entirety. In the case of inconsistencies, the present disclosure, including definitions, will control.

Definitions

As used herein, the term "carbonyl moiety" refers to any chemical moiety comprising a carbonyl functional group, e.g., a ketone, aldehyde, carboxylic acid, acid halide, amide, peptide, anhydride and ester.

As used herein, the term "heteroatom" includes nitrogen, oxygen and sulfur, as well as any atom other than a carbon.

As used herein, "fused or polycyclic ring system" refers to a saturated or unsaturated cyclic compound. "Fused ring system" refers to cyclic compounds wherein at least two adjacent carbon centers join one or more cyclic structures, e.g., compounds represented by the formulas:

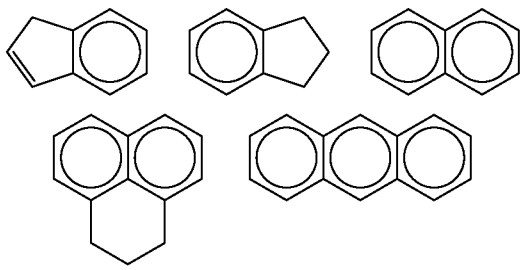

As used herein, "polycyclic ring system" refers to a compound having two or more cyclic compounds bonded in tandem, e.g., compounds represented by the formula:

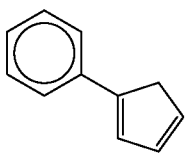

Additionally, fused or polycyclic ring systems may optionally be substituted by one or more heteroatoms, halogens, $C_1$ to $C_{12}$ alkyl, aryl, vinyl, alkyl(aryl), vinyl(aryl) and nitro groups.

Similarly, as used herein, the term "ring system" refers to a saturated or unsaturated cyclic compound, which may be optionally substituted by one or more heteroatoms, halogens, $C_1$ to $C_{12}$ alkyl, aryl, vinyl, alkyl(aryl), vinyl(aryl) and nitro groups.

As used herein, the term "primary, secondary, or tertiary amine" refers to amine compounds having one, two, or three functional groups, respectively, including, but not limited to, heteroatoms, halogens, $C_1$ to $C_{12}$ alkyl, aryl, vinyl, alkyl (aryl), vinyl(aryl) and nitro groups.

Further, as used herein, the term "hydrazone" refers to the reaction product of an aldehyde or ketone and hydrazine ($NH_2NH_2$). For example, a hydrazone may be represented by the formula:

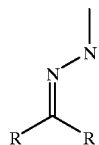

wherein R may be hydrogen or alkyl. In a preferred embodiment, the hydrazone is represented by the formula:

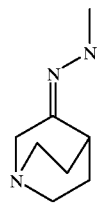

The present invention is directed to pharmaceutical formulations comprising aryldiamine compounds of generic structure (I):

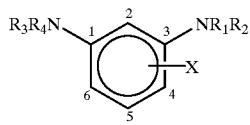

(a) wherein $R_1$, $R_2$, $R_3$, and $R_4$ are independently selected from the group consisting of hydrogen, branched or straight-chained $C_1$ to $C_{12}$ alkyl, aryl, vinyl, alkyl(aryl), vinyl(aryl), primary, secondary, or tertiary amine, amide;

(b) X is hydrogen, $NO_2$, CN, halogen, OH, $SO_2$, branched or straight-chained $C_1$–$C_6$ alkyl, alkoxy, or vinyl, positioned on the aromatic ring at any of positions 2, 4, 5 or 6;

(c) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, $R_1$, $R_2$, $R_3$, and $R_4$ are optionally interrupted with at least one heteroatom, or optionally substituted with a hydroxy, halogen, nitro, trihalomethyl group, carbonyl moiety, a substituted or unsubstituted, branched or straight-chained $C_1$ to $C_{12}$ alkyl, aryl, vinyl, alkyl(aryl), vinyl(aryl), primary, secondary, or tertiary amine, hydrazone, alkoxy, or aryloxy; or (d) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, optionally at least one of $R_1$ and $R_2$, together, and $R_3$ and $R_4$, together, form a ring system, wherein the ring system is optionally interrupted by at least one heteroatom, and optionally substituted with a hydroxy, halogen, nitro, trihalomethyl group, carbonyl moiety, $C_1$ to $C_{12}$ alkyl, primary, secondary, or tertiary amine, alkoxy, or aryloxy;

or a salt thereof, and a pharmaceutically acceptable carrier or diluent.

In one embodiment, the invention is directed to the pharmaceutical formulations comprising a compound of structure (I) wherein X is $NO_2$ positioned at the 4-position of the aromatic ring, $R_1$ and $R_3$ are hydrogen, $R_2$ is —$CH_2CH_2OC_6H_5$, and $R_4$ is —$CH_2CH_2NH_2$; or $R_3$ is hydrogen, $R_4$ is —$CH_2CH_2NH_2$, and $NR_1R_2$ is

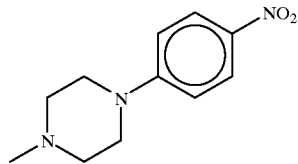

The present invention also provides methods for inhibiting microbial replication and preventing and/or treating microbial infections in an animal, comprising administering an antibacterial effective amount of the pharmaceutical formulations of the invention to an animal in need of such treatment.

The following are particular species of the generic formulas identified above:
  A. $N^1$-(2-aminoethyl)-4-nitro-$N^3$-(2-phenoxyethyl)-1,3-benzenediamine; and
  B. $N^1$-{4-nitro-3-[4-(nitrophenyl)-1-piperazinyl]phenyl}-1,2-ethanediamine.

A general procedure for the preparation of aryldiamine derivatives is set forth below.

For symmetrical aryldiamines a general procedure is as follows: to a solution of commercially available 1,3 diaminobenzene

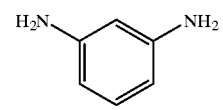

in a suitable organic solvent chosen from a group consisting of aromatic, ethereal, dimethylformamide and halogenated hydrocarbons, is optionally added a base chosen from a group consisting of trialkylamines, cyclic amines, aromatic amines, pyridine and alkali metal bases, at least 2 equivalents. To this solution is then added reagents chosen from a group consisting of alky halides and acyl halides, at least 2 equivalents, to afford the symmetrical N1, N3 disubstituted 1, 3-aryldiamines.

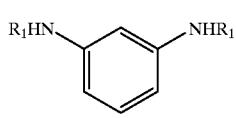

(2)

the symmetrical N1,N3 disubstituted 1,3 aryldiamines (2) may be further reacted with reagents chosen from a group consisting of alky halides and acyl halides in the presence of a base chosen from a group consisting of trialkylamines, cyclic amines, aromatic amines, pyridine and alkali metal bases, at least 2 equivalents in a suitable organic solvent chosen from a group consisting of aromatic, ethereal, dimethylformamide, and halogenated hydrocarbons, to afford N1,N1,N3,N3 tetra substituted 1,3 aryldiamines.

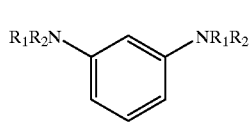

(3)

At this stage, and any of the previous stages, the aromatic ring may be functionalized utilizing chemistries described in Advanced Organic Chemistry: Fourth Edition by March, which include: reacting with a reagent chosen from a group consisting of nitric acid and sulfuric acid to afford nitrated products; bromine in the presence of ferric bromide to afford brominated products, chlorine in the presence of aluminum trichloride or acetic acid to afford chlorinated products; acyl halides in the presence of one of a group consisting of aluminum trichloride and other Lewis acids to afford acylated products; anhydrides in the presence of one of a group consisting of aluminum trichloride and other Lewis acids to afford acylated products; alkyl halides in the presence of one of a group consisting of ferric bromide, aluminum trichloride, and other Lewis acids to afford alkylated products; a reagent chosen from a group consisting of trichloroacetonitrile, bromocyanide, and mercury fulminate, to afford cyanated products; and sulfonyl halides in the presence of one of a group consisting of aluminum trichloride and other Lewis acids, to afford sulfonylated products. Phenolic derivatives may be derived from the aforementioned acyl derivatives by the use of alkaline hydrogen peroxide.

For unsymmetrical and symmetrical 1,3-aryldiamine derivatives a general procedure is as follows: commercially available mono acrylanilides

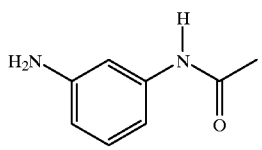

(4)

dissolved in a suitable organic solvent chosen from a group consisting of aromatic, ethereal, dimethylformamide, and halogenated hydrocarbons is optionally added a base chosen from a group consisting of trialkylamines, cyclic amines, aromatic amines, pyridine and alkali metal bases, at least 1 equivalent. To this solution is then added a reagent chosen from a group consisting of alky halides and acyl halides, at least 1 equivalent, to afford N1 substituted acrylanilides.

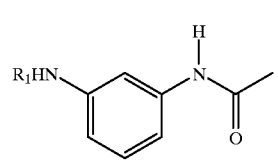

(5)

The resultant N1 substituted acrylanilides (5) can then be substituted again if desired by dissolving in a suitable organic solvent chosen from a group consisting of aromatic, ethereal, dimethylformamide, and halogenated hydrocarbons. To the resulting solution is added a base chosen from a group consisting of trialkylamines, cyclic amines, aromatic amines, pyridine and alkali metal bases, at least 1 equivalent. To this solution is then added a reagent chosen from a group consisting of alky halides and acyl halides, at least 1 equivalent to afford the N1,N1 disubstituted acrylanilides.

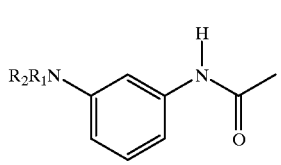

(6)

The resultant product is then hydrolyzed with aqueous base to afford the free 3-amines.

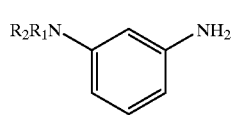

(7)

The free amine may then be dissolved in a suitable organic solvent chosen from a group consisting of aromatic, ethereal, dimethylformamide, and halogenated hydrocarbons. A base chosen from a group consisting of trialkylamines, cyclic amines, aromatic amines, pyridine, and alkali metal bases is optionally added at least 1 equivalent. To this solution is then added a reagent chosen from a group consisting of alky halides and acyl halides, at least 1 equivalent to afford N1,N1,N5, trisubstituted aryldiamines.

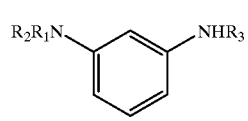

(8)

The resultant N1,N1,N3, trisubstituted aryidiamines (8) can then be substituted again if desired by dissolving in a suitable organic solvent chosen from a group consisting of aromatic, ethereal, dimethylformamide, and halogenated hydrocarbons. To the resulting solution is added a base chosen from a group consisting of trialkylamines, cyclic amines, aromatic amines, pyridine, and alkali metal bases, at least 1 equivalent. To this solution is then added a reagent chosen from a group consisting of alky halides and acyl halides, at least 1 equivalent to afford the N1,N1,N3,N3, tetra substituted aryldiamines.

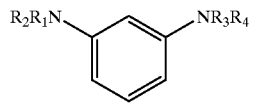

(9)

At this stage, and any of the previous intermediate stages, the aromatic ring may be functionalized utilizing chemistries described in *Advanced Organic Chemistry: Fourth Edition* by March, which include: reacting with a reagent chosen from a group consisting of nitric acid and sulfuric acid to afford nitrated products; bromine in the presence of ferric bromide to afford brominated products; chlorine in the presence of aluminum trichloride or acetic acid to afford chlorinated products; acyl halides in the presence of one of a group consisting of aluminum trichloride and other Lewis acids to afford acylated products; anhydrides in the presence of one of a group consisting of aluminum trichloride and other Lewis acids to afford acylated products; alkyl halides in the presence of one of a group consisting of ferric bromide, aluminum trichloride, and other Lewis acids to afford alkylated products; a reagent chosen from a group consisting of trichloroacetonitrile, bromocyanide, and mercury fulminate, to afford cyanated products; and sulfonyl halides in the presence of one of a group consisting of aluminum trichloride and other Lewis acids, to afford sulfonylated products. Phenolic derivatives may be derived from the aforementioned acyl derivatives by the use of alkaline hydrogen peroxide.

The present disclosure is broadly directed to a chemical process for the efficient production of aryldiamine derivatives useful as antibacterial agents. More specifically the production of N'-{4-nitro-3-[4-(nitrophenyl)-1-piperazinyl]phenyl}-1,2-ethanediamine (8)

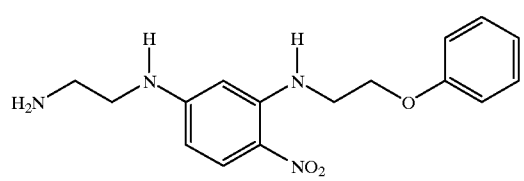

and N1-(2-aminoethyl)-4-nitro-N³-(2-phenoxyethyl)-1,3-benzenediamine.

(12)

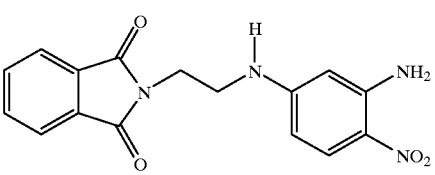

A. Production of N1-{4-nitro-3-[4-(nitrophenyl)-1-piperazinyl]phenyl}-1,2-ethanediamine (8):

To a commercially available mono acrylanilide (1)

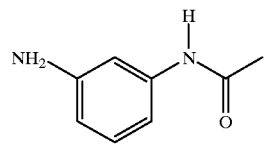

dissolved in a suitable organic solvent chosen from a group consisting of aromatic, ethereal, dimethyl formamide, and halogenated hydrocarbons is optionally added a base chosen from a group consisting of trialkylamines, cyclic tertiary amines, pyridine and alkali metal bases, at least 1 equivalent. To this solution is then added commercially available N-phthaloyl-2 bromoethylamine (2)

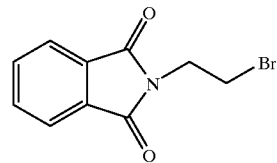

to afford N1 substituted acrylanilides.

(3)

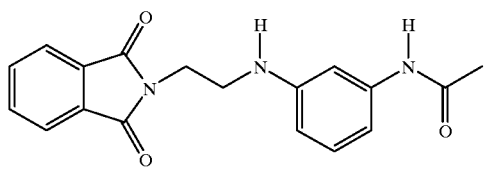

At this stage (3) is nitrated at the 4 position by the action of nitric acid and sulfuric acid to afford (4)

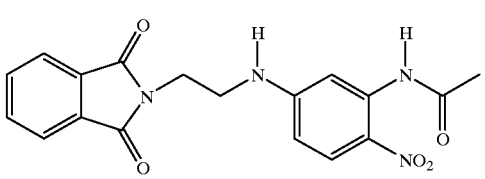

Hydrolysis of (4) by the action of an aqueous alkali base affords (5)

(5) is then dialkylated with dihalide

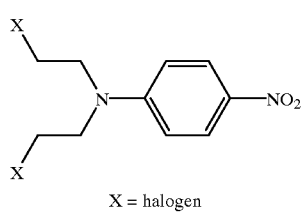

X = halogen in the presence of a base chosen from a group consisting of trialkylamines, cyclic tertiary amines, pyridine and alkali metal bases, at least 2 equivalents to afford

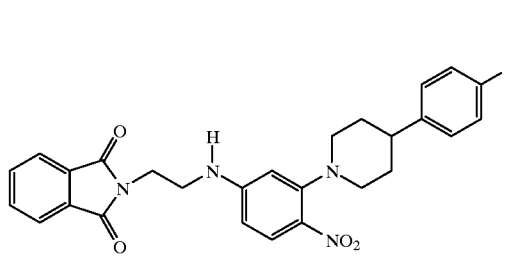

Dihalide (6) can be synthesized from the condensation of commercially available 4-nitro aniline and 2 equivalents of 2-iodo ethanol in the presence of a base chosen from a group consisting of trialkylamines, cyclic tertiary amines, pyridine and alkali metal bases, at least 2 equivalents, to afford diol

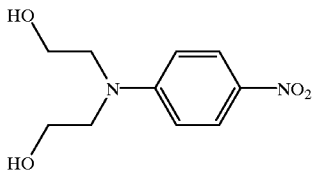

which then can be halogenated with a reagent chosen from a group consisting of thionyl chloride, carbon tetrabromide, phosphorous oxychloride, phosphorous trichloride, phosphorous tribromide, phosphorous pentachloride, and phosphorous pentabromide to afford dihalide (6). (7) is then reacted with hydrazine to afford N1-{4-(nitrophenyl)-1-piperazinyl]phenyl-1,2 -ethanedinediamine (8).

B. Production of $N^1$-(2-aminoethyl)-4-nitro-$N^3$-(2-phenoxyethyl)-1,3-benzenediamine: Commercially available mono acrylanilides (1) are dissolved in a suitable organic solvent chosen from a group consisting of aromatic, ethereal, dimethylformamide, and halogenated hydrocarbons. A base chosen from a group consisting of trialkylamines, cyclic tertiary amines, pyridine and alkali metal bases is optionally added at least 1 equivalent. To this solution is then added commercially available N-phthaloyl-2-bromoethylamine to afford N1 substituted acrylanilides. At this stage (3) is nitrated at the 4 position by the action of nitric acid and sulfuric acid to afford (4). Hydrolysis of (4) by the action of an aqueous alkali base affords (5). (5) is then alkylated with halide

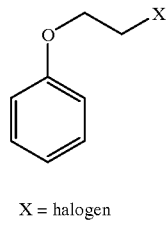

X = halogen (9) in the presence of a base chosen from a group consisting of trialkylamines, cyclic tertiary amines, pyridine and alkali metal bases, at least 1 equivalent, to afford (10).

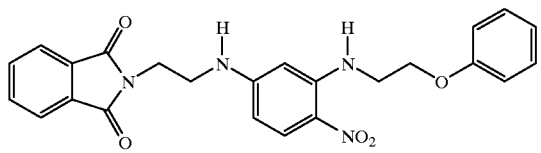

Halide (9) can be synthesized in the following manner: phenol is first reacted with an alkali metal base to form an alkali phenoxide which is then reacted with ethylene oxide to form the phenoxy alcohol (11).

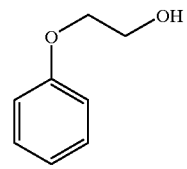

(11) can then be halogenated with a reagent chosen from a group consisting of thionyl chloride, carbon tetrabromide, phosphorous oxychloride, phosphorous trichloride, phosphorous tribromide, phosphorous pentachloride, and phosphorous pentabromide to afford halide (9). (10) is then reacted with hydrazine to afford $N^1$-(2-aminoethyl)-4-nitro-$N^3$-(2-phenoxyethyl)-1,3-benzenediamine (12).

The pharmaceutical formulations of the present invention comprise the compounds disclosed herein, which exhibit antibacterial activity. Without wishing to be bound by theory, it is believed that the antimicrobial activity of the compounds is due at least in part to their ability to inhibit microbial RNA polymerase enzymatic activity. Useful compounds may be identified by their ability to bind to and/or inhibit the enzymatic activity of, RNA polymerase from any microbial source, preferably bacterial. Compounds that exhibit RNA polymerase inhibitory activity in vitro can then be tested for in vivo antimicrobial activity. Alternatively, the antimicrobial activity of a compound may be tested directly. Identification of RNA Polymerase Inhibitors The compounds useful for inclusion in the pharmaceutical formulations of the invention can be identified by their ability to bind to, and/or inhibit the activity of, one or more bacterial RNA polymerases. RNA polymerase as used herein refers to DNA-dependent RNA polymerase holoenzyme, which is a complex consisting of five protein subunits: two copies of the α subunit and one copy each of the β, β', σ and α, β and β' subunits. The α, β and β' subunits are invariant in a given bacterial species and together form core RNA polymerase.

Binding assays

The ability of a candidate antimicrobial compound to bind to RNA polymerase can be measured using any method known in the art. Typically, purified RNA polymerase holoenzyme, or individual subunits thereof, are contacted with a plurality of compounds, and binding is monitored. Useful methods for measuring binding include without limitation those disclosed in U.S. Pat. Nos. 5,585,277 and 5,679,582.

b. Functional assays

RNA polymerase inhibition activity of a compound can be detected by including the compound in an in vitro transcription reaction and comparing the level of transcription that occurs in the presence and absence of the compound. The RNA polymerase may be from a bacterial source or, as a control, from an animal source. A typical transcription reaction (50$\mu$l) contains transcription buffer (50 mM Tris-HCl, pH 8.0, 200 mM KCl, 10 mM MgCl$_2$,10 mM DTT and 1.5 $\mu$M BSA); 1 $\mu$g of DNA template; 4 $\mu$M UTP containing 5 $\mu$Ci of [$\alpha$-$^{2-32}$P] UTP; 400 $\mu$M each of ATP, GTP, and CTP; and RNA polymerase. After incubation for 60 minutes at 25° C., the reaction is terminated with 100 $\mu$l 10% TCA, which also precipitates the newly transcribed RNA, and incorporation of radioactivity into RNA is quantified. The IC$_{50}$ (expressed in $\mu$g/ml) is the concentration of a compound that inhibits RNA polymerase activity by 50%. Candidate antimicrobial compounds are identified as those that cause a detectable inhibition of RNA polymerase activity (i.e., exhibit an lC$_{50}$ of at least 16 $\mu$g/ml).

Measurement of Antimicrobial Activity:

The antimicrobial activity of a compound or formulation according to the invention is determined by exposing a culture comprising a bacterial species to different concentrations of the compound or formulation and monitoring the effects on growth relative to a control culture not exposed to the compound. Any method known in the art may be used to assess bacterial growth. Antimicrobial effects are expressed as Minimal Inhibitory Concentration (MIC) and Minimum Bactericidal Concentration (MBC).

a. MIC

The minimal inhibitory concentration (MIC) is defined as the lowest concentration of antimicrobial agent that completely inhibits growth of the organism in the microtiter plate. The MIC may be expressed as a range between the concentration at which no growth is observed and the concentration of the dilution which immediately follows.

Typically, MIC is measured using a broth microdilution assay as follows. Dilution of candidate antimicrobial compounds in culture medium is performed in a sterile, covered 96-well microtiter plate with flat bottom wells (Costar #9017). The final concentrations of the compounds are typically 100, 50, 25, 12.5, 6.25, 3.12, 1.56, 0.78, 0.39, 0.20, 0.10, and 0.05 $\mu$g/mL, respectively. Culture medium only (containing no bacteria) is also included as a negative control for each plate. Ampicillin and rifampin are used as positive controls against all bacterial strains in every experiment.

The overnight culture of a single colony is diluted in sterile medium so that, after inoculation, each well contains approximately 5×10$^5$ CFU/mL. Within 15 minutes of preparation, 50 mL of the adjusted inoculum suspension is added to the microliter plate. Each well is diluted with an equal volume of the antimicrobial compounds or control solution. The inoculated microtiter plate is typically incubated at 35° C. for 16–20 hours. The turbidity of each well is determined by measuring the absorbance at 595 nm using a BioRad Model 3550-UV microplate reader.

Antimicrobial compounds are those that exhibit an MIC of at least 16 $\mu$g/ml.

b. MBC

The minimum bactericidal concentration (MBC) is defined as the concentration of antimicrobial agent from which no colonies grow on petri plates or in the medium. In practice, the MBC is arbitrarily defined as the concentration at which a 1000-fold reduction in colony forming units is observed with respect to the original inoculum (survival of 0.1%). Typically, the wells from a MIC microliter plate are made using a 96-well inoculation grid into a fresh microliter plate containing 100 $\mu$L Mueller-Hinton broth per well. The MBC plates are incubated at 37° C. for 16–20 hrs and the MBC values are determined.

Antimicrobial compounds are those that exhibit an MBC of at least 16 $\mu$g/ml.

Specificity determinations:

It will be understood that useful antimicrobial compositions and formulations act selectively on microbial pathogens. In vitro and/or in vivo criteria may used to determine specificity. That is, the inhibitory activity of a particular compound towards an animal RNA polymerase may be measured in parallel with a bacterial RNA polymerase. Preferably, antimicrobial compounds exhibit an lC$_{50}$ for mammalian, e.g., human, RNA Polymerase II that is at least ten-fold higher (i.e., less effective) than that for a bacterial RNA polymerase.

Furthermore, the effect of the compositions on animal cells is measured. Cytotoxicity (TD$_{50}$) is expressed as the concentration at which 50% of the cells are dead. Preferably, antimicrobial compounds according to the invention exhibit a TD$_{50}$ of less than about 5.

Methods for Preventing and Treating Microbial Infections

The present invention provides methods for inhibiting the replication of microorganisms, which comprise contacting a microorganism with an amount of an aryldiamine derivative sufficient to inhibit its growth. The invention also provides methods for preventing or treating microbial infection in an animal, which comprise administering to an animal in need of antimicrobial treatment an antimicrobial-effective amount of a composition or formulation comprising an aryldiamine derivative disclosed herein.

As used herein, the term "treatment" with regard to a microbial infection includes preventing, retarding, and/or reducing a disease, pathological condition or one or more symptoms thereof, in animals, particularly mammals, and most particularly humans. An antimicrobial effective amount is an amount that results in any improvement in one or more clinical or histological symptoms or diagnostic markers observed by a medical practitioner or determined by quantitative or semiquantitative techniques. Non-limiting examples of appropriate techniques include without limitation analysis of blood and urine. Any suitable assay may be used for determining antimicrobial effective amounts without undue experimentation, taking into account the route of administration and the age, sex, weight, species and condition of the particular patient.

Usually, a daily dosage of active ingredient can be from about 0.5 to about 100 mg per kg of body weight, preferably from about 5 to about 50 mg per kg per day and most preferably from about 10 to about 25 mg per kg per day. The total dosage may be administered in multiple doses or in a sustained release form. The dosages may be increased when treating severe or life-threatening infections.

In practicing the methods of the invention, aryldiamine derivatives can be administered by any means that produces contact of the active agent with bacteria in the body of an animal. They can be administered by any conventional means, including without limitation oral, mucosal, intranasal, parenteral, topical, subcutaneous, intradermal, intramuscular, and intravenous routes.

The compounds and formulations of the present invention may be used for prevention and treatment of a wide variety of bacterial infections, including without limitation diseases of the skin, e.g., endocarditis, acne and skin ulcers; gastroenteritis; colitis; meningitis; keratinitis; conjunctivitis; diseases of the urinary and genital tracts, e.g., syphilis and gonorrhea; breast disease (mastitis); osteomyelitis; otitis; as well as diseases of the lungs, e.g. pneumonia and tuberculosis. The compounds are generally active in treating diseases caused by Staphylococcus aureus. In addition, the compounds are valuable for sterilizing the gut in the course of surgery.

Pharmaceutical Formulations

The present invention provides pharmaceutical formulations comprising the aryldiamine derivatives disclosed herein in conjunction with a pharmaceutically acceptable carrier or diluent.

The formulations of the present invention can be solutions, suspensions, emulsions, syrups, elixirs, capsules, tablets, and the like. The compositions may contain a suitable carrier, diluent, or excipient, such as sterile water, physiological saline, glucose, or the like. Moreover, the formulations can also be lyophilized, and/or may contain auxiliary substances, such as wetting or emulsifying agents, pH buffering agents, adjuvants, gelling or viscosity enhancing additives, preservatives, flavoring agents, colors, and the like, depending upon the route of administration and the preparation desired. Standard texts, such as "Remington's Pharmaceutical Science", 17th Ed., 1985, incorporated herein by reference, may be consulted to prepare suitable preparations, without undue experimentation.

The formulations can include powdered carriers, such as lactose, sucrose, mannitol, starch, cellulose derivatives, magnesium stearate, stearic acid, and the like. Further, tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. The formulations can also contain coloring and flavoring to enhance patient acceptance.

In general, water, a suitable oil, saline, aqueous dextrose (glucose), and related sugar solutions and glycols such as propylene glycol or polyethylene glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances.

Antioxidants such as, for example, sodium bisulfate, sodium sulfite, citric acid and its salts, sodium EDTA, ascorbic acid, and the like can be used either alone or in combination with other suitable antioxidants or stabilizing agents typically employed in the pharmaceutical compositions. In addition, parenteral solutions can contain preservatives, such as, for example, benzalkonium chloride, methyl- or propyl-paraben, chlorobutanol and the like.

The formulations can also include any of disintegrants, lubricants, plasticizers, colorants, and dosing vehicles. Suitable pharmaceutical carriers are described in Remington's Pharmaceutical Sciences, A. Osol, a standard reference text in this field.

In order for a composition to be administered to an animal or human, and for any particular method of administration, it is preferred to determine the toxicity, such as by determining the MIC and MBC (see above) in a suitable animal model, e.g., mouse; the dosage of the composition(s), and the concentration of components in the composition; and the timing of administration in order to maximize the antimicrobial response. Such factors can be determined without undue experimentation by such methods as titrations and analysis of sera for antibodies or antigens, e.g., by ELISA and/or EFFIT analysis. Such determinations do not require undue experimentation from the knowledge of the skilled artisan, the present disclosure and the documents cited herein.

Suitable formulations typically contain from about 1 to about 1000 mg of active ingredient per dosage unit. In these pharmaceutical compositions, the active ingredient will ordinarily be present in an amount of about 0.5 to about 95%, by weight, based on the total weight of the composition.

The following are intended as non-limiting examples of the invention.

EXAMPLE 1

Biological Activity of Aryldiamines

The following experiments were performed to evaluate the biological activity of the following benzoquinoline compounds disclosed herein.

(A) $N^1$-(2-aminoethyl)-4-nitro-$N^3$-(2-phenoxyethyl)-1,3-benzenediamine; and (B) $N^1$-{4-nitro-3-[4-(nitrophenyl)-1-piperazinyl]phenyl}-1,2-ethanediamine.

a. In vitro:

The compounds of the invention were included at a range of concentrations in in vitro transcription reactions containing purified RNA polymerase derived from either S. aureus, E. coli, or human, and template DNA comprising a pTaq promoter. The reaction conditions and analytical method are described above.

The concentration of each compound that inhibited RNA polymerase activity by 50%, i.e., the $IC_{50}$, is shown in Table 1.

| | Class II (Aryl diamine) | | | |
|---|---|---|---|---|
| | | (A) | (B) | Amp | Rif |
| $IC_{50}$ (µg/ml) | S. aureus | 4 | 4 | | |
| | E. coli | 8 | 9 | | |
| | human pol II | 100 | 40 | | |
| MIC (µg/ml) | S. aureus | 6 | 1 | 8 | <0.03 |
| | $rif^R$-S. aureus | 13 | 2 | 4 | >64 |
| | E. coli | 13 | 8 | 2 | 4 |
| | E. coli* | 13 | 4 | 0.13 | <0.03 |
| MBC (µg/ml) | S. aureus | 25 | 8 | | |
| | $rif^R$-S. aureus | 25 | 8 | | |
| | E. coli | 50 | 32 | | |
| | E. coli* | 25 | 2 | | |

The results indicated that both of the compounds selectively inhibited bacterial RNA polymerase relative to human RNA polymerase; in both cases, S. aureus RNA polymerase was the most sensitive to the inhibitory effects of the compounds. Compound (A) exhibited the highest degree of selectivity for bacterial RNA polymerases.

b. In vivo:

The antimicrobial activities of the compounds of the invention, expressed as MIC and MBC, were determined as described above, using as tester strains wild-type *S. aureus*, rifampicin-resistant *S. aureus*, wild-type *E. coli*, and *E. coli* cells that had been permeabilized.

Compound (B) exhibited the most potent antimicrobial activity against *S. aureus* but was less effective against *E. coli*.

What is claimed is:

1. A pharmaceutical composition comprising a compound of the formula

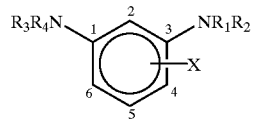

(a) wherein $R_1$, $R_2$, $R_3$, and $R_4$ are independently selected from the group consisting of hydrogen, branched or straight-chained $C_1$ to $C_{12}$ alkyl, aryl, vinyl, alkyl(aryl), vinyl(aryl), primary, secondary, or tertiary amine, amide;

(b) X is hydrogen, $NO_2$, CN, halogen, OH, $SO_2$, branched or straight-chained $C_1$–$C_6$ alkyl, alkoxy, or vinyl, positioned at any of positions 2, 3, 4 or 6 of the aromatic ring;

(c) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, $R_1$, $R_2$, $R_3$, and $R_4$ are optionally interrupted with at least one heteroatom, or optionally substituted with a hydroxy, halogen, nitro, trihalomethyl group, carbonyl moiety, a substituted or unsubstituted, branched or straight-chained $C_1$ to $C_{12}$ alkyl, aryl, vinyl, alkyl(aryl), vinyl(aryl), primary, secondary, or tertiary amine, hydrazone, alkoxy, or aryloxy; and (d) wherein when $R_1$, $R_2$, $R_3$, and $R_4$ are branched or straight-chained $C_1$ to $C_{12}$ alkyl, aryl, vinyl, alkyl(aryl), vinyl(aryl), primary, secondary, or tertiary amine or amide, optionally at least one of $R_1$ and $R_2$, together, and $R_3$ and $R_4$, together, form a ring system, wherein the ring system is optionally interrupted by at least one heteroatom, and optionally substituted with a hydroxy, halogen, nitro, trihalomethyl group, carbonyl moiety, $C_1$ to $C_{12}$ alkyl, primary, secondary, or tertiary amine, alkoxy, or aryloxy;

or a salt thereof, and a pharmaceutically acceptable carrier or diluent.

2. The pharmaceutical composition of claim 1 wherein $R_1$ and $R_3$ are hydrogen, $R_2$ is —$CH_2CH_2OC_6H_5$, $R_4$ is —$CH_2CH_2NH_2$, and X is $NO_2$ positioned at the 4-position of the aromatic ring.

3. The pharmaceutical composition of claim 1 wherein $R_3$ is hydrogen, $R_4$ is —$CH_2CH_2NH_2$, $NR_1R_2$ is

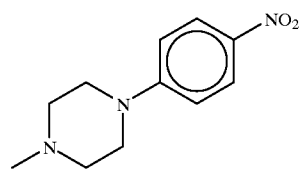

and X is $NO_2$ positioned at the 4-position of the aromatic ring.

4. The pharmaceutical composition of claim 1 wherein the compound is selected from the group consisting of
$N^1$-(2-amirloethyl)-4-nitro-$N^3$-(2-phenoxyethyl)-1,3-benzenediamine; and
$N^1$-{4-nitro-3-[4-(nitrophenyl)-1-piperzinyl]phenyl}-1,2-ethanediamine.

5. A method for inhibiting microbial replication comprising contacting a microorganism with an effective amount of at least one pharmaceutical composition of claim 1 to inhibit its growth.

6. A method for preventing and/or treating microbial infections in an animal, comprising administering to an animal in need of antimicrobial treatment an antimicrobial effective amount of at least one pharmaceutical composition of claim 1.

* * * * *